United States Patent
Sugito (10) Patent No.: US 9,921,200 B2
(45) Date of Patent: Mar. 20, 2018

(54) OXYGEN DETECTING MULTILAYER BODY, AS WELL AS OXYGEN DETECTING PACKAGING MATERIAL AND OXYGEN ABSORBER PACKAGE USING THE SAME

(71) Applicant: MITSUBISHI GAS CHEMICAL COMPANY, INC., Tokyo (JP)

(72) Inventor: Ken Sugito, Okayama (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 132 days.

(21) Appl. No.: 14/898,205

(22) PCT Filed: Jun. 18, 2014

(86) PCT No.: PCT/JP2014/066198
§ 371 (c)(1),
(2) Date: Dec. 14, 2015

(87) PCT Pub. No.: WO2014/203942
PCT Pub. Date: Dec. 24, 2014

(65) Prior Publication Data
US 2016/0146767 A1    May 26, 2016

(30) Foreign Application Priority Data
Jun. 21, 2013 (JP) .................. 2013-130923

(51) Int. Cl.
*G01N 21/75* (2006.01)
*G01N 31/22* (2006.01)
*B65D 79/02* (2006.01)

(52) U.S. Cl.
CPC ........... *G01N 31/225* (2013.01); *B65D 79/02* (2013.01)

(58) Field of Classification Search
CPC .............................. G01N 31/225; B65D 79/02
See application file for complete search history.

(56) References Cited

U.S. PATENT DOCUMENTS

2005/0089682 A1    4/2005  Su et al.

FOREIGN PATENT DOCUMENTS

| CN | 202079845 | 12/2011 |
|----|-----------|---------|
| CN | 102380989 | 3/2012 |

(Continued)

OTHER PUBLICATIONS

International Preliminary Examination Report in PCT/JP2014/066198, dated Dec. 30, 2015.

(Continued)

*Primary Examiner* — Dennis White
(74) *Attorney, Agent, or Firm* — Greenblum & Bernstein, P.L.C.

(57) ABSTRACT

An oxygen detecting multilayer body allows easy detection of a color change of an oxygen detecting layer, and prevention of crazing of an oxygen detecting layer. The oxygen detecting multilayer body includes a transparent resin layer, a heat seal layer, and an oxygen detecting layer containing an oxygen detecting component, placed occupying a part of a space between the transparent resin layer and the heat seal layer, wherein a spacer is placed to occupy at least a part of a space between the transparent resin layer and the heat seal layer, where the oxygen detecting layer is not provided, so as to make up a missing thickness of the oxygen detecting multilayer body, wherein the thickness of the oxygen detecting layer is from 0.5 to 40 μm, and the ratio of the thickness of the oxygen detecting layer to the thickness of the spacer is from 15:1 to 1:10.

20 Claims, 2 Drawing Sheets

(56) References Cited

FOREIGN PATENT DOCUMENTS

| | | | |
|---|---|---|---|
| JP | 05-149943 | | 6/1993 |
| JP | 2003-227797 | | 8/2003 |
| JP | 2003-307513 | | 10/2003 |
| JP | 2003307513 A | * | 10/2003 |
| JP | 2003-322648 | | 11/2003 |
| JP | 2006-17650 | | 1/2006 |
| JP | 2006017650 A | * | 1/2006 |
| JP | 2006-96394 | | 4/2006 |
| JP | 2007-192779 | | 8/2007 |
| JP | 2008-032689 | | 2/2008 |
| JP | 2008-224391 | | 9/2008 |
| JP | 4742879 | | 5/2011 |
| TW | 201118375 A | | 6/2011 |

OTHER PUBLICATIONS

Extended European Search Report issued in Patent Application No. 14813276.4, dated Feb. 22, 2017.
Search Report in International Patent Application No. PCT/JP2014/066198, dated Sep. 16, 2014.

* cited by examiner

OXYGEN DETECTING MULTILAYER BODY, AS WELL AS OXYGEN DETECTING PACKAGING MATERIAL AND OXYGEN ABSORBER PACKAGE USING THE SAME

BACKGROUND OF THE INVENTION

Technical Field

The present invention relates to an oxygen detecting multilayer body having an oxygen detecting function. More particularly, it relates to an oxygen detecting multilayer body, which can easily detect a color change of an oxygen detecting layer, and prevent an oxygen detecting layer from crazing. The invention further relates to an oxygen detecting packaging material using the oxygen detecting multilayer body and an oxygen absorber package packaged by the oxygen detecting packaging material.

Background Art

With respect to various articles which are susceptible to oxygen induced alteration or deterioration, such as a food, a beverage, a drug, a medical article, a cosmetic, a metal product, and an electronic product, an oxygen absorber is used for removing oxygen in a hermetic container keeping such an article, for purpose of storing the same for a long period while preventing oxidation deterioration.

Among various kinds of oxygen absorbers, there is an oxygen absorber with an oxygen detecting agent. An oxygen absorber with an oxygen detecting agent is an oxygen absorber in a sachet form or a sheet form, to which an oxygen detecting agent is attached, and when the inside of a hermetic container becomes in a deoxidized state, such an oxygen concentration in the hermetic container can be visually recognized through a color change of the oxygen detecting agent.

Heretofore, as an oxygen detecting agent an oxidation-reduction dye such as methylene blue has been used. However, an oxidation-reduction dye such as methylene blue is easily deteriorated by light irradiation. Therefore, it has been proposed to place an anchor coat layer or an overcoat layer imparted with a light screening property adjacent to an oxygen indicator layer using an oxidation-reduction dye (refer to Patent Literature 1). Further, since the dyeing power of methylene blue is so strong, that the same tends to migrate to the content, when the two are in contact tightly. Consequently, it has been proposed to place a transparent resin layer not allowing permeation of methylene blue, on an oxygen detecting layer (refer to Patent Literature 2).

CITATION LIST

Patent Literature

[Patent Literature 1] Japanese Unexamined Patent Application Publication No. 2003-227797
[Patent Literature 2] Japanese Unexamined Patent Application Publication No. 2006-017650

SUMMARY OF THE INVENTION

Technical Problem

The inventors diligently investigated the background art to find that, in a case in which an oxygen detecting layer is placed by gravure printing as in Patent Literature 2, a production cost can be reduced owing to a simplified process, however, the thickness of the oxygen detecting layer cannot exceed a certain value, and therefore detection of a color change of the oxygen detecting layer becomes difficult. When the thickness of an oxygen detecting layer was managed to be thicker than the conventional thickness, detection of a color change of the oxygen detecting layer could be made easier. However, a new problem has come to be known: since a part where an oxygen detecting layer is placed becomes thicker than other parts, when an oxygen detecting multilayer body is wound up to a roll for example for transportation, the thicker part with an oxygen detecting layer comes to bear a load, and the oxygen detecting layer may craze.

The present invention was made in view of such background art and the newly found problems with an object to provide an oxygen detecting multilayer body which allows easy detection of a color change of an oxygen detecting layer and prevents an oxygen detecting layer from crazing.

Solution to Problem

The inventors studied diligently for achieving the object to find that this can be achieved by placing a spacer to occupy at least a part of a space where the oxygen detecting layer is not provided so as to make up a missing thickness of an oxygen detecting multilayer body. The present invention was completed based on the finding.

Namely, the present invention provides the following inventions (1) to (20).

(1) An oxygen detecting multilayer body comprising:
a transparent resin layer,
a heat seal layer, and
an oxygen detecting layer containing an oxygen detecting component, placed occupying a part of a space between the transparent resin layer and the heat seal layer,
wherein a spacer is placed to occupy at least a part of a space between the transparent resin layer and the heat seal layer, where the oxygen detecting layer is not provided, so as to make up a missing thickness of the oxygen detecting multilayer body,
wherein the thickness of the oxygen detecting layer is from 0.5 to 40 μm, and
the ratio of the thickness of the oxygen detecting layer to the thickness of the spacer is from 15:1 to 1:10.
(2) The oxygen detecting multilayer body according to (1) above, wherein a spacer is not provided between the transparent resin layer and the oxygen detecting layer.
(3) The oxygen detecting multilayer body according to (1) or (2) above, wherein the percentage of the surface area of the spacer with respect to the overall surface area of the oxygen detecting multilayer body is from 10 to 99.7%.
(4) The oxygen detecting multilayer body according to any one of (1) to (3) above, wherein the ratio of the surface area of the spacer to the surface area of the oxygen detecting layer is from 0.6:1 to 332:1.
(5) The oxygen detecting multilayer body according to any one of (1) to (4) above, wherein the percentage of the surface area of the oxygen detecting layer with respect to the overall surface area of the oxygen detecting multilayer body is from 0.3 to 15%.
(6) The oxygen detecting multilayer body according to any one of (1) to (5) above, wherein a first sealing layer not allowing permeation of the oxygen detecting component is provided between the transparent resin layer and the oxygen detecting layer.
(7) The oxygen detecting multilayer body according to any one of (1) to (6) above, wherein a second sealing layer not allowing permeation of the oxygen detecting component is provided between the oxygen detecting layer and the heat seal layer.

(8) The oxygen detecting multilayer body according to (7) above, wherein an adhesive layer is provided between the second sealing layer and the heat seal layer.

(9) The oxygen detecting multilayer body according to any one of (1) to (8) above, wherein the spacer does not allow permeation of the oxygen detecting component.

(10) The oxygen detecting multilayer body according to any one of claims (1) to (9) above, wherein the spacer allows permeation of oxygen.

(11) The oxygen detecting multilayer body according to any one of (1) to (10) above, wherein the oxygen detecting component comprises at least one kind selected from the group consisting of a thiazine dye, an azine dye, an oxazine dye, an indigoid dye, and a thioindigoid dye.

(12) The oxygen detecting multilayer body according to any one of (1) to (11) above, wherein the transparent resin layer comprises at least one kind of resin selected from the group consisting of polyethylene terephthalate, polypropylene, and nylon.

(13) The oxygen detecting multilayer body according to any one of (1) to (12) above, wherein the heat seal layer comprises at least one kind of resin selected from the group consisting of polyethylene, polypropylene, an ethylene-vinyl acetate copolymer resin, and an ethylene-(meth)acrylate copolymer resin.

(14) The oxygen detecting multilayer body according to any one of (1) to (13) above, wherein the oxygen detecting layer comprises at least one kind of resin selected from the group consisting of a cellulose resin, polyurethane, an acrylic resin, and polyvinyl alcohol.

(15) The oxygen detecting multilayer body according to any one of (6) to (14) above, wherein the first sealing layer and/or the second sealing layer comprises independently at least one kind of resin selected from the group consisting of polyurethane, polyolefin, a nitrocellulose resin, and an acrylic resin.

(16) The oxygen detecting multilayer body according to any one of (1) to (15) above, wherein the spacer is in contact with the oxygen detecting layer.

(17) The oxygen detecting multilayer body according to any one of (1) to (15) above, wherein the spacer is apart from the oxygen detecting layer.

(18) An oxygen detecting packaging material utilizing at least partly the oxygen detecting multilayer body according to any one of (1) to (17) above.

(19) An oxygen absorber package having packaged an oxygen absorber composition with the oxygen detecting packaging material according to (18) above.

(20) A method for producing the oxygen detecting multilayer body according to any one of (1) to (17) above comprising:

a step for layering an oxygen detecting layer containing an oxygen detecting component on a transparent resin layer by gravure printing, a step for layering a spacer on the transparent resin layer at a part, where the oxygen detecting layer is not provided, by gravure printing, and a step for layering a heat seal layer on the oxygen detecting layer and the spacer.

Advantageous Effects of Invention

An oxygen detecting multilayer body according to the present invention allows easy detection of a color change of an oxygen detecting layer and can prevent an oxygen detecting layer from crazing. Further, by providing a spacer in an oxygen detecting multilayer body according to the present invention, even when the percentage of the surface area of an oxygen detecting layer with respect to the overall surface area of the oxygen detecting multilayer body is selected small in order to reduce the consumption of an expensive oxygen detecting component, crazing of the oxygen detecting layer can be prevented.

DESCRIPTION OF EMBODIMENTS

Oxygen Detecting Multilayer Body

An oxygen detecting multilayer body according to the present invention comprises a transparent resin layer, a heat seal layer, and an oxygen detecting layer, placed occupying a part of a space between the transparent resin layer and the heat seal layer, wherein a spacer is placed to occupy at least a part of a space between the transparent resin layer and the heat seal layer, where the oxygen detecting layer is not provided, so as to make up a missing thickness of the oxygen detecting multilayer body. An oxygen detecting multilayer body according to the present invention may further comprise a first sealing layer between the transparent resin layer and the oxygen detecting layer, may further comprise a second sealing layer between the oxygen detecting layer and the heat seal layer, and may further comprise an adhesive layer between the second sealing layer and the heat seal layer.

Figure 1:
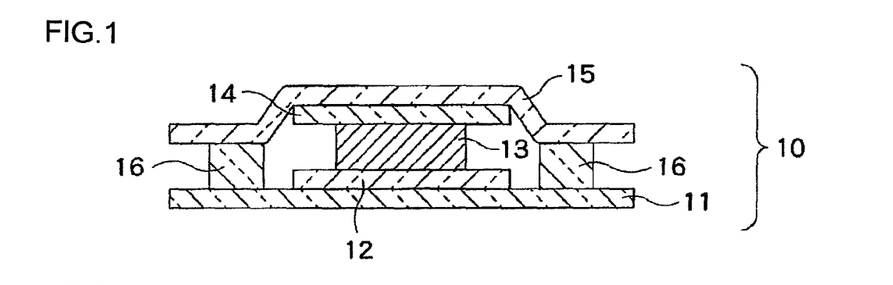
FIG. 1 is a schematic sectional view showing an Embodiment of an oxygen detecting multilayer body according to the present invention.

A sectional view of an Embodiment of an oxygen detecting multilayer body according to the present invention is shown in FIG. 1. According to an aspect of the present invention, an oxygen detecting multilayer body 10 is provided, in which a transparent resin layer 11, a first sealing layer 12, an oxygen detecting layer 13, a second sealing layer 14, and a heat seal layer 15 are layered one on another in the order mentioned; and a spacer 16 is provided apart from the oxygen detecting layer 13 at a part of a space between the transparent resin layer 11 and the heat seal layer 15, where the oxygen detecting layer 13 is not provided. Each layer of an oxygen detecting multilayer body according to the present invention and a component thereof will be described below in detail.

Transparent Resin Layer

A transparent resin layer according to the present invention is a layer to be positioned on the outer surface of an oxygen detecting packaging material including an oxygen detecting multilayer body, and is preferably formed of a material having permeability of oxygen and being superior in visibility of an oxygen detecting layer. The oxygen permeability of a transparent resin layer is preferably 1 mL/(m$^2$·atm·day) or more, and more preferably 10 mL/(m$^2$·atm·day) or more. As such a material, for example, use of at least one kind of resin selected from the group consisting of polyethylene terephthalate, polypropylene, and nylon is preferable. A transparent resin layer preferably does not allow permeation of an oxygen detecting component for the sake of prevention of solving out to the exterior of an oxygen detecting component. The thickness of the transparent resin layer is ordinarily from 5 to 100 μm, and preferably from 10 to 50 μm.

Heat Seal Layer

A heat seal layer according to the present invention is a layer to be positioned on the internal surface of an oxygen detecting packaging material including an oxygen detecting multilayer body, and is preferably formed of a material having permeability of oxygen. The oxygen permeability of a transparent resin layer is preferably 1×10$^3$ mL/(m$^2$·atm·day) or more, and more preferably 2×10$^3$ mL/(m$^2$·atm·day) or more. As such a material, for example, use of at least one kind of resin selected from the group consisting of polyethylene, polypropylene, an ethylene-vinyl acetate copolymer resin, and an ethylene-(meth)acrylate copolymer resin is preferable. A heat seal layer preferably does not allow permeation of an oxygen detecting component for the sake of prevention of migration of an oxygen detecting component to a content. The thickness of the heat seal layer is ordinarily from 5 to 100 μm, and preferably from 10 to 80 μm.

Oxygen Detecting Layer

An oxygen detecting layer according to the present invention has a function for detecting oxygen, and contains an oxygen detecting component. As an oxygen detecting component, a color-changeable organic colorant is used. A color-changeable organic colorant is an aromatic compound including a long conjugated double bond system having n electrons mobile in a molecule, which is a compound changing the color reversibly by oxidation-reduction. As a color-changeable organic colorant, an oxidation-reduction indicator, as well as a thiazine dye, an azine dye, an oxazine dye, an indigoid dye, and a thioindigoid dye are favorably used. Examples thereof include methylene blue, new methylene blue, methylene green, Variamine blue B, diphenyl amine, ferroin, capri blue, safranine T, indigo, indigo carmine, indigo white, and indirubin. A thiazine dye represented by methylene blue is preferable.

Further, by adding separately a non-color-changing colorant deferent from an oxygen detecting composition to the oxygen detecting composition, a color change can be made clear. As such a colorant, a pigment or a dye, which is not sensitive to an oxidation-reduction reaction, and exhibits a color contrasting to a color of a color-changeable organic colorant in an aerobic state and a color of the same in an anaerobic state, may be used. When blue-coloring methylene blue is used as a color-changeable organic colorant, examples of an appropriate non-color-changing colorant include acid red and phloxine B, which are red-color food additives.

The thickness of an oxygen detecting layer is from 0.5 to 40 μm, preferably from 1 to 30 μm, more preferably from 2 to 25 μm, and further preferably from 4 to 20 μm. When the thickness of an oxygen detecting layer is approximately within the range, a color change of an oxygen detecting layer can be detected easily.

An oxygen detecting layer can be formed by a publicly known printing method using an ink mixing an oxygen detecting component with a binder resin or a solvent. As a printing process, for example, but not limited to, a gravure printing method or a screen printing method may be used.

Figure 6:
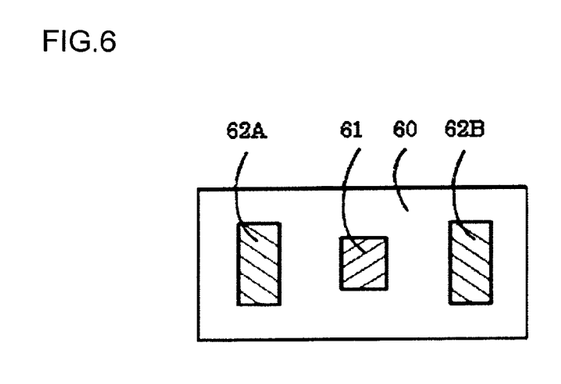
FIG. 6 is a schematic plan view showing an Embodiment of an oxygen detecting multilayer body according to the present invention.

An oxygen detecting layer is placed to occupy at least a part of a space between a transparent resin layer and a heat seal layer. Since an oxygen detecting component is expensive, it is required to reduce the percentage of the surface area of an oxygen detecting layer with respect to the overall surface area of an oxygen detecting multilayer body (hereinafter also expressed simply as "surface area ratio of an oxygen detecting layer"). However, if a surface area ratio of an oxygen detecting layer is made smaller, the oxygen detecting layer is pressed at a higher load, and crazing occurs more likely. By providing a spacer described below, a surface area ratio of an oxygen detecting layer may be regulated in a range preferably from 0.3 to 15%, more preferably from 0.5 to 10%, and especially preferably from 2 to 5%. If regulated in the above preferable range, the oxygen detecting layer is prevented from crazing, and at the same time the consumption of an expensive oxygen detecting component can be curtailed. A surface area in the present invention represents a surface area in a plan view (a drawing seen in the layering direction) of an oxygen detecting multilayer body. In this regard, a schematic plan view of an Embodiment of an oxygen detecting multilayer body according to the present invention is shown in FIG. 6. The surface area of the overall surface area of an oxygen detecting multilayer body in FIG. 6 is the area of the oxygen detecting multilayer body 60, and the surface area of an oxygen detecting layer is the area of the oxygen detecting layer 61.

Spacer

A spacer according to the present invention is for occupying at least a part of a space where an oxygen detecting layer is not provided so as to make up a missing thickness of an oxygen detecting multilayer body. A spacer may be formed to contact any of a transparent resin layer, a heat seal layer, and a sealing layer, insofar as the same makes up a missing thickness of an oxygen detecting multilayer body. Further, it is preferable that a spacer is not provided between a transparent resin layer and an oxygen detecting layer. When there is not a spacer between an outer transparent resin layer and an oxygen detecting layer, the visibility of the oxygen detecting layer can be improved.

A spacer may be in contact with an oxygen detecting layer or apart from an oxygen detecting layer. When a spacer is apart from an oxygen detecting layer, the gap between a spacer and an oxygen detecting layer is preferably from 0.05 to 25 mm, and more preferably from 0.1 to 20 mm. So long as the gap between a spacer and an oxygen detecting layer is approximately within the range, the entire oxygen detecting multilayer body becomes so flat, that a load impressed on the oxygen detecting layer can be reduced even when an oxygen detecting multilayer body is wound up to a roll, and that the oxygen detecting layer can be prevented from crazing.

The ratio of the thickness of an oxygen detecting layer to the thickness of a spacer is from 15:1 to 1:10, preferably from 13:1 to 1:5, further preferably from 10:1 to 1:2, and especially preferably from 5:1 to 1:1. When the thickness of an oxygen detecting layer to the thickness of a spacer is approximately within the range, a missing thickness of an oxygen detecting multilayer body can be covered at a part where an oxygen detecting layer is not provided. As the result, the thickness difference between a part where an oxygen detecting layer is provided and a part where an oxygen detecting layer is not provided is moderated and the entire oxygen detecting multilayer body becomes so flat, that a load impressed on the oxygen detecting layer can be reduced, even when an oxygen detecting multilayer body is wound up to a roll, and that the oxygen detecting layer can be prevented from crazing. Further, detachment of a print during winding up of a film can be also prevented.

The percentage of the surface area of a spacer with respect to the overall surface area of an oxygen detecting multilayer body (hereinafter also expressed simply as "surface area ratio of a spacer") is preferably from 10 to 99.7%, more preferably from 30 to 99.5%, and further preferably from 50 to 99%. When the surface area ratio of a spacer is approximately within the range, an oxygen detecting layer can be prevented from crazing and the cost can be reduced. In this regard, in a case in which spacers are placed at a plurality of locations, the surface area of a spacer means the total surface areas of the spacers. The surface area of the overall surface area of an oxygen detecting multilayer body in FIG. 6 is the area of the oxygen detecting multilayer body 60, and the surface area of a spacer is the sum of the area of the spacer 62A and the area of the spacer 62B.

The ratio of the surface area of a spacer to the surface area of an oxygen detecting layer is preferably from 0.6:1 to 332:1, more preferably from 5:1 to 100:1, and further preferably 10:1 to 50:1. When the ratio of the surface area of a spacer to the surface area of an oxygen detecting layer is approximately within the range, an oxygen detecting layer can be prevented from crazing and the cost can be reduced.

There is no particular restriction on a material for forming a spacer, and similar materials as in the case of other layers, such as a transparent resin layer, a heat seal layer, and a sealing layer, may be used. For example, it is preferable to form a spacer with a material similar to that used for a sealing layer, because the spacer does not allow permeation of an oxygen detecting component. It is also preferable to form a spacer with a material similar to that used for a heat seal layer because the spacer becomes oxygen-permeable.

A spacer may contain a colored ink. By coloring a spacer, a color change of an oxygen detecting layer can be recognized more easily. A colored ink has preferably a light color for the sake of improvement of the visibility of an oxygen detecting layer. Examples of a light color include gray, white, yellow, beige, and pink. Especially gray and white are preferable. Examples of a colorant to be used for a colored ink include an inorganic pigment, an organic pigment, a metallic pigment, a fluorescent pigment, and a dye. The above may be used singly, or in a mixture of 2 or more kinds thereof. As a colorant to be used for a white ink, a white pigment, such as titanium oxide, zinc oxide, zirconium oxide, an alumina powder, magnesium oxide, and zinc sulfide, may be used favorably. A gray color can be prepared by adding a black ink to a white ink.

Sealing Layer

According to the present invention, a first sealing layer is a layer for preventing an oxygen detecting component from solving out to the exterior, and a second sealing layer is a layer for preventing an oxygen detecting component from migrating into a content. It is preferable that the first sealing layer and the second sealing layer are respectively formed from at least one kind of resin selected from the group consisting of polyurethane, polyolefin, a nitrocellulose resin, and an acrylic resin. The first sealing layer and the second sealing layer may be formed respectively from the different resins, or the same resin. The thickness of a sealing layer is ordinarily from 0.1 to 3 µm, and preferably from 0.2 to 2 µm.

The second sealing layer may contain a colored ink, such as a white pigment and a yellow pigment, in order to make a color change of an oxygen detecting layer more conspicuous. Alternatively, a layer containing a colored ink may be provided between an oxygen detecting layer and the second sealing layer.

Adhesive Layer

An adhesive layer according to the present invention is an adhesive layer or an adhesive resin layer to be formed for bonding any 2 layers, such as a second sealing layer and a heat seal layer, for lamination. For example, adhesives for lamination including a solvent type, a water type, and an emulsion type; a one-pack type, and a two-pack type; a curing type and a non-curable type; a vinyl-base, a (meth) acrylic-base, a polyamide-base, a polyester-base, a polyether-base, a polyurethane-base, an epoxy-base, a rubber-base, and similar lamination adhesives may be used. The adhesive may be applied by a publicly known method, such as a gravure roll coating method, a kiss coating method, a reverse roll coat method, a fountain coating method, and a transfer roll coating method.

As an adhesive resin layer, a resin layer composed of a thermoplastic resin layer may be used. Specific examples of a material to be used for an adhesive resin layer include a low density polyethylene resin, a medium density polyethylene resin, a high density polyethylene resin, a linear low density polyethylene resin, an ethylene/α-olefin copolymer resin polymerized using a metallocene catalyst, an ethylene/polypropylene copolymer resin, an ethylene/vinyl acetate copolymer resin, an ethylene/acrylic acid copolymer resin, an ethylene/ethyl acrylate copolymer resin, an ethylene/methacrylic acid copolymer resin, an ethylene/methyl methacrylate copolymer resin, an ethylene/maleic acid copolymer resin, an ionomer resin, a resin from a polyolefin resin graft-polymerized, or copolymerized with an unsaturated carboxylic acid, an unsaturated carboxylic acid, an unsaturated carboxylic anhydride, or an ester monomer, and a resin from a polyolefin resin graft-modified with maleic anhydride. The materials may be used singly or in combination of two or more kinds thereof.

Pattern Layer

An oxygen detecting multilayer body according to the present invention may further include a pattern layer. A pattern layer should be preferably placed on the content side of a transparent resin layer, and may be, for example, placed between a transparent resin layer and a first sealing layer, or between a transparent resin layer and a spacer. As a pattern layer, for example, a letter, or a mark formed by a printing ink may be used.

Method for Producing Oxygen Detecting Multilayer Body

A method for producing an oxygen detecting multilayer body according to the present invention comprises a step for layering an oxygen detecting layer containing an oxygen detecting component on a transparent resin layer by gravure printing, a step for layering a spacer on the transparent resin layer at a part, where the oxygen detecting layer is not provided, by gravure printing, and a step for layering a heat seal layer on the oxygen detecting layer and the spacer. A production method according to the present invention may further comprise a step for layering a first sealing layer by gravure printing on a transparent resin layer before layering an oxygen detecting layer. Further, a production method according to the present invention may further comprise a step for layering a second sealing layer by gravure printing on an oxygen detecting layer before layering a heat seal layer, or comprise a step for layering an adhesive layer on a second sealing layer.

Oxygen Detecting Packaging Material

An oxygen detecting packaging material according to the present invention utilizes at least partly the oxygen detecting multilayer body. An oxygen detecting packaging material may be produced by joining two heat seal layers of an oxygen detecting multilayer body followed by heat-sealing. An oxygen detecting packaging material may be used as a packaging material for various articles including foods in combination with a publicly known oxygen concentration reducing means (oxygen absorber, nitrogen replacement, reduced pressure deaeration, etc.). Further, as described below, an oxygen absorber composition can be packaged using an oxygen detecting packaging material to an oxygen absorber package.

Oxygen Absorber Package

An oxygen absorber package according to the present invention is an oxygen absorber composition packaged with the oxygen detecting packaging material. There is no particular restriction on an oxygen absorber composition, and a publicly known composition may be used. Examples of an oxidizable substance include a metal powder such as an iron powder, an organic compound such as ascorbic acid, and a polymer having a carbon-carbon double bond. Heretofore, a system in which an oxygen absorber composition is enclosed in a packaging material, and a separate oxygen detecting agent is bonded on to the packaging material (a so-called oxygen absorber with an oxygen detecting agent) has been used. In the case of an oxygen absorber package according to the present invention, an oxygen detecting layer is incorporated in a packaging material for an oxygen absorber, and therefore it is not necessary to bond separately an oxygen detecting agent so that the number of production steps as well as the relevant costs can be reduced.

EXAMPLES

The present invention will be described in detail by way of Examples, provided that the present invention be not limited to the following Examples. In this regard, among the substances used in Examples, for methylene blue, D-fructose, magnesium hydroxide, ethylene glycol, isopropyl alcohol (hereinafter referred to as "IPA"), and ethyl acetate, reagents prepared by Wako Pure Chemical Industries, Ltd. were used.

Example 1

As a transparent resin layer, a 12 μm-thick PET film (trade name: E5100, produced by Toyobo Co., Ltd.) was prepared. On the PET film, a 1 μm-thick urethane-base resin was layered as a first sealing layer by gravure printing (trade name: CLIOS Medium, produced by DIC Graphics Corporation). An ink for an oxygen detecting layer described below was printed in twice by gravure printing on the first sealing layer to form a 20 μm-thick oxygen detecting layer. The surface area of the oxygen detecting layer was set at 4% with respect to the surface area of the PET film. Further, on the transparent resin layer at a location where the first sealing layer is not formed, and at a position apart from the oxygen detecting layer, an ink for a spacer (gray (black+white), trade name: LAMIC SR) was printed by gravure printing to provide a 10 μm-thick spacer. The gap between the spacer and the oxygen detecting layer was 2 mm. The percentage of the surface area of the spacer was 85% with respect to the surface area of the PET film, and the ratio of the surface area of the spacer to the surface area of the oxygen detecting layer was 85:4. Next, on the oxygen detecting layer a urethane-base resin with the same thickness of 1 μm-thick as the first sealing layer was layered by gravure printing as a second sealing layer. On the second sealing layer, a 30 μm-thick LLDPE film (trade name: TUX-TCS, produced by Mitsui Chemicals Tohcello, Inc.) was dry-laminated as a heat seal layer by the intermediary of an adhesive. A schematic sectional view of the obtained oxygen detecting multilayer body was as shown in FIG. 1.

The composition for an ink for an oxygen detecting layer was decided as follows. In this regard, as phloxine B, Food Red No. 104 produced by Hodogaya Chemical Co., Ltd. was used, and as a cellulose acetate propionate resin, CAP504-0.2 (trade name, produced by Eastman Chemical Company) was used.

| | |
|---|---|
| methylene blue | 0.5 part by mass |
| phloxine B | 0.4 part by mass |
| D-fructose | 5 parts by mass |
| magnesium hydroxide | 15 parts by mass |
| ethylene glycol | 5 parts by mass |
| cellulose acetate propionate resin | 5 parts by mass |
| mix solution of IPA (50 mass-%) and ethyl acetate (50 mass-%) | 70 parts by mass |

Example 2

An oxygen detecting multilayer body was produced identically with Example 1 except that the thickness of a spacer was changed to 20 μm.

Example 3

An oxygen detecting multilayer body was produced identically with Example 1 except that the thickness of a spacer was changed to 5 μm.

Example 4

An oxygen detecting multilayer body was produced identically with Example 1 except that the thickness of an oxygen detecting layer was changed to 5 μm.

Example 5

An oxygen detecting multilayer body was produced identically with Example 1 except that the thickness of an oxygen detecting layer was changed to 10 μm.

Example 6

Figure 2:
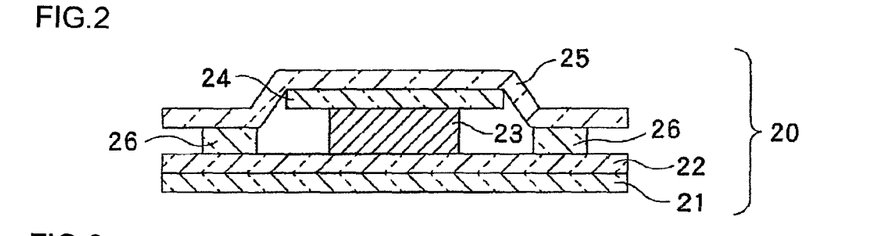
FIG. 2 is a schematic sectional view showing an Embodiment of an oxygen detecting multilayer body according to the present invention.

An oxygen detecting multilayer body was produced identically with Example 1 except that a spacer with a thickness of 10 μm is formed on the first sealing layer and at a position apart from the oxygen detecting layer by printing an ink for spacer described below by gravure printing. A schematic sectional view of the obtained oxygen detecting multilayer body was as shown in FIG. 2.

Example 7

Figure 3:
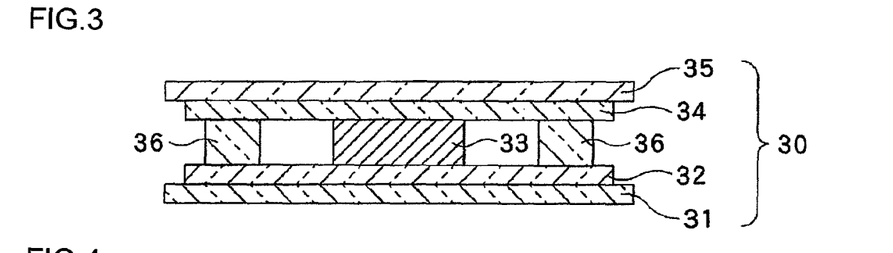
FIG. 3 is a schematic sectional view showing an Embodiment of an oxygen detecting multilayer body according to the present invention.

An oxygen detecting multilayer body was produced identically with Example 6 except that a second sealing layer was layered on the oxygen detecting layer and the spacer. A schematic sectional view of the obtained oxygen detecting multilayer body was as shown in FIG. 3.

Example 8

Figure 4:
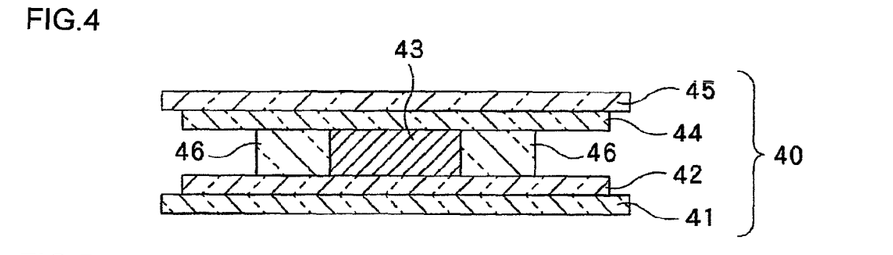
FIG. 4 is a schematic sectional view showing an Embodiment of an oxygen detecting multilayer body according to the present invention.

An oxygen detecting multilayer body was produced identically with Example 7 except that a spacer was provided on the first sealing layer and at a position in contact with the oxygen detecting layer. A schematic sectional view of the obtained oxygen detecting multilayer body was as shown in FIG. 4.

Comparative Example 1

An oxygen detecting multilayer body was produced identically with Example 1 except that a spacer was not provided.

Comparative Example 2

An oxygen detecting multilayer body was produced identically with Example 1 except that the thickness of the spacer was changed to 1 μm.

Comparative Example 3

An oxygen detecting multilayer body was produced identically with Example 1 except that the thickness of the oxygen detecting layer was changed to 0.4 μm, and a spacer was not provided.

TABLE 1

Figure 5:
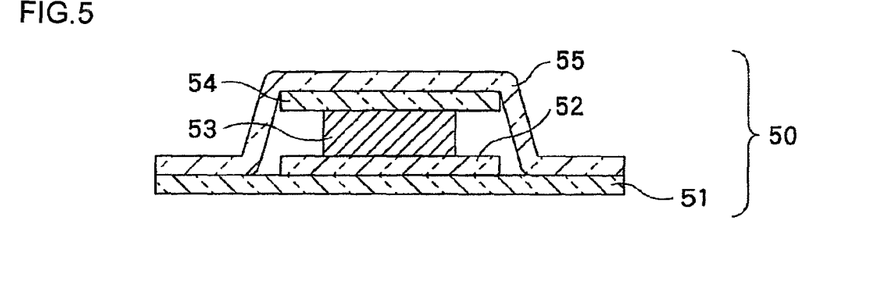
FIG. 5 is a schematic sectional view showing an Embodiment of oxygen detecting multilayer bodies according to Comparative Examples 1 and 3.

|  | Thickness of oxygen detecting layer | Thickness of spacer | Ratio of thickness of oxygen detecting layer to thickness of spacer | Schematic sectional view *1 |
| --- | --- | --- | --- | --- |
| Example 1 | 20 | 10 | 2:1 | FIG. 1 |
| Example 2 | 20 | 20 | 1:1 | FIG. 1 |
| Example 3 | 20 | 5 | 4:1 | FIG. 1 |
| Example 4 | 5 | 10 | 1:2 | FIG. 1 |
| Example 5 | 10 | 10 | 1:1 | FIG. 1 |
| Example 6 | 20 | 10 | 2:1 | FIG. 2 |
| Example 7 | 20 | 10 | 2:1 | FIG. 3 |
| Example 8 | 20 | 10 | 2:1 | FIG. 4 |
| Comparative Example 1 | 20 | 0 | — | FIG. 5 |
| Comparative Example 2 | 20 | 1 | 20:1 | FIG. 1 |
| Comparative Example 3 | 0.4 | 0 | — | FIG. 5 |

*1 The schematic sectional views indicate a relative positional relationship between an oxygen detecting layer and a spacer.
The ratios of the thickness of an oxygen detecting layer to the thickness of a spacer in the schematic sectional views do not necessarily correspond to actual thickness ratios in the respective Examples and Comparative Examples.

Evaluation Test

The following evaluation tests were conducted on the oxygen detecting multilayer bodies produced as above.

Evaluation of Winding Property

Each of the oxygen detecting multilayer bodies produced as above was wound up to a roll and the appearance of the oxygen detecting layer was evaluated visually according to the following criteria. The evaluation results are shown in Table 2.

Evaluation Criteria

◯: There appeared no crazing in an oxygen detecting layer.

x: There appeared crazing in an oxygen detecting layer.

Evaluation of Visibility

Each of the oxygen detecting multilayer bodies produced as above was left standing in the atmosphere, and a color change of an oxygen detecting layer was evaluated visually according to the following criteria. The evaluation results are shown in Table 2.

Evaluation Criteria

◯: A color change of an oxygen detecting layer was detected clearly.

x: A color change could be detected, but there was recognizable ink detachment due to ink cracking.

x x: A color change of an oxygen detecting layer was hardly detected.

TABLE 2

|  | Evaluation of winding property | Evaluation of visibility |
| --- | --- | --- |
| Example 1 | ◯ | ◯ |
| Example 2 | ◯ | ◯ |
| Example 3 | ◯ | ◯ |
| Example 4 | ◯ | ◯ |
| Example 5 | ◯ | ◯ |
| Example 6 | ◯ | ◯ |
| Example 7 | ◯ | ◯ |
| Example 8 | ◯ | ◯ |
| Comparative Example 1 | x | x |
| Comparative Example 2 | x | ◯ |
| Comparative Example 3 | ◯ | x x |

REFERENCE SIGNS LIST

10 Oxygen detecting multilayer body
11 Transparent resin layer
12 first sealing layer
13 Oxygen detecting layer
14 second sealing layer
15 Heat seal layer
16 Spacer
20 Oxygen detecting multilayer body
21 Transparent resin layer
22 first sealing layer
23 Oxygen detecting layer
24 second sealing layer
25 Heat seal layer
26 Spacer
30 Oxygen detecting multilayer body
31 Transparent resin layer
32 first sealing layer
33 Oxygen detecting layer
34 second sealing layer
35 Heat seal layer
36 Spacer
40 Oxygen detecting multilayer body
41 Transparent resin layer
42 first sealing layer
43 Oxygen detecting layer
44 second sealing layer
45 Heat seal layer
46 Spacer
50 Oxygen detecting multilayer body
51 Transparent resin layer
52 first sealing layer
53 Oxygen detecting layer
54 second sealing layer
55 Heat seal layer 60 Oxygen detecting multilayer body
61 Oxygen detecting layer
62A Spacer
62B Spacer

The invention claimed is:

1. An oxygen detecting multilayer body comprising:
a transparent resin layer,
a heat seal layer, and
an oxygen detecting layer containing an oxygen detecting component, placed occupying a part of a space between the transparent resin layer and the heat seal layer,
wherein a spacer is placed to occupy at least a part of a space between the transparent resin layer and the heat seal layer, where the oxygen detecting layer is not provided, so as to make up a missing thickness of the oxygen detecting multilayer body,
wherein a thickness of the oxygen detecting layer is from 4 to 40 μm, and
a ratio of the thickness of the oxygen detecting layer to the thickness of the spacer is from 15:1 to 1:10.

2. The oxygen detecting multilayer body according to claim 1, wherein a spacer is not provided between the transparent resin layer and the oxygen detecting layer.

3. The oxygen detecting multilayer body according to claim 1, wherein the percentage of the surface area of the spacer with respect to the overall surface area of the oxygen detecting multilayer body is from 10 to 99.7%.

4. The oxygen detecting multilayer body according to claim 1, wherein the ratio of the surface area of the spacer to the surface area of the oxygen detecting layer is from 0.6:1 to 332:1.

5. The oxygen detecting multilayer body according to claim 1, wherein the percentage of the surface area of the oxygen detecting layer with respect to the overall surface area of the oxygen detecting multilayer body is from 0.3 to 15%.

6. The oxygen detecting multilayer body according to claim 1, wherein a first sealing layer not allowing permeation of the oxygen detecting component is provided between the transparent resin layer and the oxygen detecting layer.

7. The oxygen detecting multilayer body according to claim 1, wherein a second sealing layer not allowing permeation of the oxygen detecting component is provided between the oxygen detecting layer and the heat seal layer.

8. The oxygen detecting multilayer body according to claim 7, wherein an adhesive layer is provided between the second sealing layer and the heat seal layer.

9. The oxygen detecting multilayer body according to claim 1, wherein the spacer does not allow permeation of the oxygen detecting component.

10. The oxygen detecting multilayer body according to claim 1, wherein the spacer allows permeation of oxygen.

11. The oxygen detecting multilayer body according to claim 1, wherein the oxygen detecting component comprises at least one kind selected from the group consisting of a thiazine dye, an azine dye, an oxazine dye, an indigoid dye, and a thioindigoid dye.

12. The oxygen detecting multilayer body according to claim 1, wherein the transparent resin layer comprises at least one kind of resin selected from the group consisting of polyethylene terephthalate, polypropylene, and nylon.

13. The oxygen detecting multilayer body according to claim 1, wherein the heat seal layer comprises at least one kind of resin selected from the group consisting of polyethylene, polypropylene, an ethylene-vinyl acetate copolymer resin, and an ethylene-(meth)acrylate copolymer resin.

14. The oxygen detecting multilayer body according to claim 1, wherein the oxygen detecting layer comprises at least one kind of resin selected from the group consisting of a cellulose resin, polyurethane, an acrylic resin, and polyvinyl alcohol.

15. The oxygen detecting multilayer body according to claim 6, wherein the first sealing layer and/or the second sealing layer comprises independently at least one kind kind of resin selected from the group consisting of polyurethane, polyolefin, a nitrocellulose resin, and an acrylic resin.

16. The oxygen detecting multilayer body according to claim 1, wherein the spacer is in contact with the oxygen detecting layer.

17. The oxygen detecting multilayer body according to claim 1, wherein the spacer is apart from the oxygen detecting layer.

18. An oxygen detecting packaging material utilizing at least partly the oxygen detecting multilayer body according to claim 1.

19. An oxygen absorber package having packaged an oxygen absorber composition with the oxygen detecting packaging material according to claim 18.

20. A method for producing the oxygen detecting multilayer body according to claim 1 comprising:
layering an oxygen detecting layer containing an oxygen detecting component on a transparent resin layer by gravure printing,
layering a spacer on the transparent resin layer at a part, where the oxygen detecting layer is not provided, by gravure printing, and
layering a heat seal layer on the oxygen detecting layer and the spacer.

\* \* \* \* \*

UNITED STATES PATENT AND TRADEMARK OFFICE
CERTIFICATE OF CORRECTION

PATENT NO. : 9,921,200 B2  
APPLICATION NO. : 14/898205  
DATED : March 20, 2018  
INVENTOR(S) : K. Sugito

Page 1 of 1

It is certified that error appears in the above-identified patent and that said Letters Patent is hereby corrected as shown below:

In the Claims

At Column 14, Line 25 (Claim 15, Line 3), please change "kind kind" to -- kind --.

Signed and Sealed this  
Second Day of October, 2018

Andrei Iancu  
*Director of the United States Patent and Trademark Office*